United States Patent [19]

Gates

[11] Patent Number: 5,102,447
[45] Date of Patent: Apr. 7, 1992

[54] METHODS AND COMPOSITIONS FOR PROTECTING CROP PLANTS FROM UNDESIRABLE EFFECTS OF INSECTICIDAL COMPOUNDS

[75] Inventor: Donald W. Gates, Yardley, Pa.

[73] Assignee: American Cyanamid Company, Stamford, Conn.

[21] Appl. No.: 432,651

[22] Filed: Nov. 6, 1989

Related U.S. Application Data

[63] Continuation of Ser. No. 108,250, Oct. 13, 1987, abandoned.

[51] Int. Cl.$^5$ ............................................. A01N 43/38
[52] U.S. Cl. ........................................ 71/95; 514/127; 514/417
[58] Field of Search ................. 72/96; 514/127, 417; 71/95

[56] References Cited

U.S. PATENT DOCUMENTS

| | | | |
|---|---|---|---|
| 2,596,076 | 5/1952 | Hook et al. | 167/22 |
| 2,970,080 | 1/1961 | Oros et al. | 167/22 |
| 3,940,419 | 2/1976 | Diehl et al. | 71/95 |
| 4,017,299 | 4/1977 | Diehl et al. | 71/96 |
| 4,021,228 | 5/1977 | Arneklev et al. | 71/96 |
| 4,433,997 | 2/1984 | Pallos | 71/92 |
| 4,488,898 | 12/1984 | Fory et al. | 71/96 |
| 4,695,564 | 9/1987 | Walgenbach | 514/127 |

OTHER PUBLICATIONS

Gorog et al., Herbicidal Antidot, 5-Agrochemicals Abstract, 95:145267p (1981).

Primary Examiner—Richard L. Raymond
Assistant Examiner—John D. Pak
Attorney, Agent, or Firm—John W. Hogan, Jr.

[57] ABSTRACT

The present invention relates to methods for protecting crop plants from undesirable effects of pesticides and herbicides. The roots, seeds or soil surrounding the crop plants are treated with an effective amount of phthalimide compound in conjunction with the use of an effective amount of the insecticidal compound or herbicidal compound. Compositions for so protecting crop plants also are provided.

3 Claims, No Drawings

METHODS AND COMPOSITIONS FOR PROTECTING CROP PLANTS FROM UNDESIRABLE EFFECTS OF INSECTICIDAL COMPOUNDS

This application is a continuation of copending application Ser. No. 07/108,250, filed Oct. 13, 1987, now abandoned.

BACKGROUND OF THE INVENTION

The present invention relates to methods and compositions for protecting crop plants from undesirable effects of pesticides (such as insecticides and/or herbicides). The crop plants are protected by treating the roots, seeds or soil surrounding the crop plant or the foliage thereof with an effective amount of the phthalimide compounds disclosed herein in conjunction with the use of the effective amount of the insecticide and/or herbicide.

Although many insecticidally and/or herbicidally active compounds are commercially available for the protection of agronomically important crops, the spectrum of crops in which these compounds may be employed is frequently limited due to insufficient selectivity on that given crop or because an inadequate margin of safety exists between the rates required for pesticidal activity and the rates at which undesirable effects on the crop plant are observed. The margin of safety for a given compound on a given crop may be effected by weather conditions such as extended periods of low temperature, excessive rainfall, excessive heat or dryness and soil type. Also, the use of specific compounds may be unsuitable in areas where crops are rotated, due to residual activity of the compounds on the following years crop.

The phthalimide compounds useful in the present invention and their preparation are described in U.S. Pat. No. 3,940,419, incorporated herein by reference thereto. Those phthalimide compounds and their use as plant growth regulating compounds also are described in U.S. Pat. No. 4,017,299, also incorporated herein by reference thereto. However, surprisingly, it has been found that treatment of crops with said phthalimide compounds results in safening from the phytotoxic effects encountered by treatment with a variety of pesticides, such as insecticidal and/or herbicidal compounds.

SUMMARY OF THE INVENTION

The present invention relates to methods for safening insecticidal and herbicidal treatments and compositions useful therein wherein an effective amount of a phthalimide compound having the structure

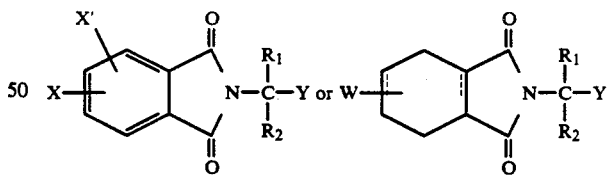

wherein W is hydrogen or alkyl $C_1$-$C_4$; X and X' each represent hydrogen, halogen, alkyl $C_1$-$C_4$, $CF_3$, alkoxy ($C_1$-$C_4$), benzyloxy, di($C_1$-$C_4$)alkylamino, $C_1$-$C_4$ alkyl thio, hydroxy, $C_1$-$C_4$ alkylsulfonyl, alkanoylamino $C_1$-$C_4$ or nitro; Y is —$COOR_3$, —$CONHR_8$, —$CONR_3R_4$, —$CONHN(R_5)_2$, —$CONHN^+(R_6)_3$ halide-, —CN or $COR_7$ with the proviso that at least one of X and X' is a substituent other than hydrogen; $R_1$ and $R_2$ each represent alkyl $C_1$-$C_4$ or when taken together with the carbon to which they are attached form cycloalkyl $C_4$-$C_{11}$ optionally substituted with methyl; $R_3$ and $R_4$ each represent hydrogen or alkyl $C_1$-$C_4$; $R_5$ and $R_6$ each represent alkyl $C_1$-$C_2$; $R_7$ is halogen and $R_8$ is —$CH_3$ or

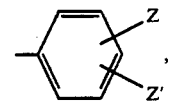

where Z and Z' are hydrogen, halogen, alkyl $C_1$-$C_2$, —$CF_3$ or —$OCH_3$; ===== is a single or double bond with the proviso that there be only 0 or 1 double bond or isomeric mixtures thereof and mixtures thereof is applied to the roots, seeds, foliage or soil surrounding an agronomically important crop plant in conjunction with the use of an effective amount of an insecticidal compound and/or a herbicidal compound.

It is an object of the present invention, therefore, to provide methods and compositions for protecting crops from the undesirable effects of insecticidal compounds and/or herbicidal compounds wherein said method comprises treating the roots, seeds, foliage or the soil surrounding the crop with an effective amount of a phthalimide compound in conjunction with the use of an effective amount of an insecticidal and/or herbicidal compound.

It is another object of this invention to provide a method for protecting crops from undesirable effects of insecticidal and herbicidal compositions, often time associated with residual activity in the soil. These and further objects of the invention will become apparent by the more detailed description of the invention provided hereinbelow.

DETAILED DESCRIPTION OF INVENTION

The present invention relates to methods for safening insecticidal and herbicidal treatments and compositions useful therein wherein an effective amount of a phthalimide compound having the structure

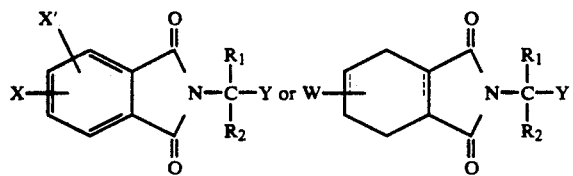

wherein W is hydrogen or alkyl $C_1$-$C_4$; and X and X' each represent hydrogen, halogen, alkyl $C_1$-$C_4$, $CF_3$, alkoxy ($C_1$-$C_4$), benzyloxy, di ($C_1$-$C_4$)alkylamino, $C_1$-$C_4$ alkylthio, hydroxy, $C_1$-$C_4$ alkylsulfonyl, alkanoylamino $C_1$-$C_4$ or nitro; Y is —$COOR_3$, —$CONHR_8$, —$CONR_3R_4$, —$CONHN(R_5)_2$, $CONHN^+(R_6)_3$ halide-, —CN or $COR_7$ with the proviso that at least one of X and X' is a substituent other than hydrogen; $R_1$ and $R_2$ each represent alkyl $C_1$-$C_4$ or when taken together with the carbon to which they are attached form cycloalkyl $C_4$-$C_{11}$ optionally substituted with methyl; $R_3$ and $R_4$ each represent hydrogen or alkyl $C_1$-$C_4$; $R_5$ and $R_6$ each represent alkyl $C_1$-$C_2$; $R_7$ is halogen and $R_8$ is —$CH_3$ or

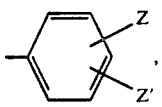

where Z and Z' are hydrogen, halogen, alkyl $C_1$–$C_2$, —$CF_3$ or —$OCH_3$; ══ is a single or double bond with the proviso that there be only 0 or 1 double bond or isomeric mixtures thereof and mixtures thereof is applied to the roots, seeds, foliage or soil surrounding an agronomically important crop plant in conjunction with the use of an effective amount of an insecticidal compound and/or a herbicidal compound.

METHOD OF USE

Treatment of crop plants such as wheat, barley, rice, corn, sorghum, cotton, soybeans and the like with phthalimide compounds at rates of about 20 ppm to 10,000 ppm results in both significantly improved early seedling vigor and improved stand establishment of the crops when compared to plants treated with high rates of insecticidal compounds and herbicidal compound alone thus providing a margin of safety to said treatments.

Preferred embodiments of this invention employ the use of 1-(3-chlorophthalamido)cyclohexanecarboxamide at rates of 50 ppm to 10,000 ppm for protection with the insecticidal and herbicidal compounds described above at insecticidally effective and herbicidally effective rates.

The method of this invention is suitable for providing a degree of protection to a variety of monocotyledonous and dicotyledonous plants from undesirable effects when insecticidal and herbicidal compounds are applied, either at excessive rates inadvertently applied or under climatic conditions which stress the plant.

Further, the method of the present invention, in several instances, allows the use of an insecticidal or herbicidal compound on a crop or in a climate that made it previously unsuitable for use due to phytotoxicity or unsatisfactory safety margin.

Insecticidal treatments benefiting by utilizing the method of the present invention include the phosphorodithioate insecticides, such as phorate on corn, cotton and sorghum, and terbufos on sorghum. Carbamate insecticides, such as aldicarb on cotton and the like also are safened by the method of the present invention.

Herbicide treatments which are currently known and which benefit by utilizing the method of the invention include:
dinitroaniline herbicides such as pendimethalin and trifluralin in corn and sorghum; AHAS (acetohydroxy acid/acetolactate synthase inhibiting herbicides such as the imidazolinone herbicides in cereal crops; substituted butanoic acids such as erythro, and threo, methyl 3-(3-(m-chlorophenyl)-4-cyano-4-(m-fluorophenyl)butyrate in rice; urea herbicides, such as isoproturon in graminacious crops such as barley and fluometuron in crops such as cotton; and plant growth regulating compounds, such as the recently-developed series of triazole compounds including paclobulrazol, uniconazol, triapenthenol and similar compounds.

Preferred phthalimides for use in the treatments and compositions of this invention are those wherein Y is $CONR_3R_4$, $CONHN(R_5)_2$, $CONHN^+(R_6)_3 \cdot halide^{\ominus}$, $CN$, $COR_7$ or $CONHR_8$.

A more preferred group of phthalimides compounds are those wherein Y is $CONR_3R_4$.

A most preferred group of phthalimide compounds includes:
1-(3-chlorophthalimido)cyclohexanhecarboxamide, 1-(3-chlorophthalimido)cyclopentanecarboxamide, 1-(4-chlorophthalimido)cyclohexanecarboxamide, 1-(4-methylphthalimido)-1-cyclohexanecarboxamide, 1-(3,4,5,6-tetrahydrophthalimido)-1-cyclohexanecarboxamide, α-isobutyl-α-methyl-α-(3-chlorophthalamido) acetamide, 1-(3-trifluoromethylphthalimido)-cyclohexanecarboxamide and 1-(3,5-dichlorophthalamido)-1-cyclohexanecarboxamide.

COMPOSITIONS

The effectiveness of the method of the present invention for protecting plant crops is not limited by formulation or method of application. The active phthalimide compounds may be formulated as dusts, dust concentrates, wettable powders, emulsifiable concentrates, soil drenches, granular formulations and the like. They may be applied in combination with a solid or liquid diluent, by a variety of methods, including root dips, seed coatings, transplant water, preplant incorporation in the soil, preemergence soil application and postemergence to crop foliage. Soil, seed and root treatments are preferred methods of protecting the present invention.

Wettable powders with individual compounds useful in the invention or combination of compounds can be prepared by blending said compound(s) with a solid carrier, such as attapulgite, kaolin, diatomaceous earth, silica, or the like, and a small amount of a dispersant and wetting agent. Then, the mixture is air-milled to effect a reduction of particle size to about 5 microns to 10 microns. A typical wettable powder might contain 50.0% on a weight basis of the active compound(s), 5.0% on a weight basis of a highly-purified partially-desulfonated sodium lignin sulfonate, 1.0% on a weight basis of sodium N-methyl-N-oleoyltaurate and 44.0% on a weight basis of attapulgite.

In practice, the active ingredient in the above composition varies from about 10% to 80% on a weight basis. However, in such cases, the solid diluent is varied accordingly.

For dust preparations such as a 10% dust, 20%, by weight, of the 50% wettable powder is blended with about 80%, by weight, of a solid carrier, such as kaolin. Equipment suitable for preparing such dusts are ribbon-type blenders and double-cone blenders. It is apparent that the concentration of the active compounds(s) in dust compositions can be varied by adjusting the amount of wettable powder and carrier used. Typical dusts contain about 0.5% to 15%, by weight, of active compound(s), although higher or lower concentrations may also be prepared.

An alternative process for preparing dusts, also dust concentrates, involves blending the active compound(s) with a solid carrier and passing the uniform blend through an attrition mill to obtain the desired particle size.

Preferably, the phthalimide compounds of the invention are applied as seed treatments in which the phthalimide compound is applied to seed in dry or wet form. Dry treatment consists of the active compound(s) in an inert dust carrier which may contain additives to prevent cohesion into lumps or stickers to improve adhesion to the seeds. Wetting agent(s) are useful so that the powder can be wetted with water and used as a slurry treatment. Wet treatments are applied by steeping the seed in a solution of active compound(s) in water or other solvent, or by a slurry method when using surfactant(s).

Low volume liquid treatments are sometimes used. In such uses, the active compounds(s) is applied as a high concentration in a suitable solvent. Such treatments avoid the problems of having to dry the seed or sowing immediately after treatment to prevent premature germination. Quick-drying emulsion treatments which allow application of very large doses also may be employed.

Other formulations, methods, products and advantages of the present invention are apparent from the examples set forth hereinabove, but these examples are provided as an illustration of the present invention and are not intended to be limiting thereof.

EXAMPLE 1

Efficacy and Safening of Treatments of the Invention with Insecticide Compounds

Seeds of sorghum, variety DK 42Y, are treated with the phthalimide compound, 1-(3-chlorophthalimido)cyclohexanecarboxamide at the indicated in Table I.

Test method: four inch plastic pots are filled to within one inch of the top with greenhouse soil and leveled to a firm seed bed. Six seeds are placed on top of the leveled soil. Insecticides are then sprinkled over the seeds at the rates shown in Table I. The pots are then filled to the top with soil and are placed in a greenhouse. Pots are initially watered overhead and then bottom watered for the duration of the experiment. Greenhouse temperatures run at 29° C. for day time and 19° C. for night times. Each treatment is replicated eight times and compared to both negative controls, which are not treated, and positive controls which are treated with the insecticide or the phthalimide compound. Nineteen days after treatment, the plants are rated for stand by counting the plants in each pot, recording average plant height, and measuring average fresh weight.

The results of these experiments are summarized in Table I.

EXAMPLE 2

Efficacy and Safening of Treatments of the Invention when using Herbicides in Rice Three to four leaf rice seedlings are dipped into solutions of the varying concentrations of 1-(3-chlorophthalimido)cyclohexanecarbamide listed in Table II below before being transplanted into 32 oz plastic pots filled with Wisconsin silt loam soil (3.5% O.M.). The pots are then flooded to a depth of about 2 cm above the soil surface. Three days after transplanting, application of the herbicide erythro and threo methyl 3-(m-chlorophenyl)-4-cyano-4-(m-fluorophenyl)butyrate is made at a rate of 1 kg/ha directly to the flood water, and the plants are set in a greenhouse and cared for by standard procedures. Three weeks after treatment, the plants are rated visually for percent injury. The results of these experiments are summarized in Table II.

TABLE II

| Herbicide | Rates | % Rice injury |
|---|---|---|
| Phthalimide compound | 153 ppm | 0 |
| Phthalimide compound | 75 ppm | 0 |
| Phthalimide compound | 38 ppm | 0 |
| Phthalimide compound | 19 ppm | 0 |
| Herbicidal compound | 1 kg/ha | 50% to 90% |
| Phthalimide + herbicide | 153 + 1 kg/ha | 0 to 10% |
| Phthalimide + herbicide | 75 + 1 kg/ha | 0 to 10% |
| Phthalimide + herbicide | 38 + 1 kg/ha | 0 |
| Phthalimide + herbicide | 19 + 1 kg/ha | 0 |

EXAMPLE 3

Efficacy and Safening of Treatments of the Invention when a Dinitroaniline Herbicide is used on Corn Seeds of corn, variety P3541, are treated with the phthalimide compound, 1-(3-chlorophthalimido)cyclohexanecarboxamide formulated as a dust, at the rates indicated in Table III.

Test method: Five inch plastic pots are filled to within one inch of the top with greenhouse soil and leveled to a firm seed bed. Five seeds are placed on top of the leveled soil, and the herbicide, pendimethalin, is applied as a spray to simulate preemergence (pre), preplant incorporated (PPI) or an infurrow (IF) applica-

TABLE I

| Treatment | Rate/pot | Plant stand/ plants | Average plant height (cm) | Average fresh wt/pot (g) |
|---|---|---|---|---|
| Phorate (granular 20%) | 25 mg | 38 | 27.3 | 2.30 |
| Phorate (granular 20%) | 50 mg | 29 | 24.1 | 1.58 |
| Phorate (granular 20%) | 100 mg | 17 | 22.3 | 0.89 |
| Phorate (20%) + phthalimide | 25 mg + 1000 ppm | 36 | 35.3 | 2.78 |
| Phorate (20%) + phthalimide | 50 mg + 1000 ppm | 35 | 31.6 | 2.56 |
| Phorate (20%) + phthalimide | 100 mg + 1000 ppm | 20 | 21.1 | 0.78 |
| Phthalmide | 1000 ppm | 37 | 38.4 | 4.54 |
| Control no treatment | 0 | 41 | 34.0 | 4.3 |
| Terbufos (granular 15%) | 40 mg | 37 | 14.57 | 7.04 |
| Terbufos (granular 15%) | 80 mg | 33 | 14.36 | 5.69 |
| Terbufos (granular 15%) | 160 mg | 31 | 10.79 | 2.88 |
| Terbufos (15%) + phthalimide | 40 mg + 500 ppm | 36 | 16.57 | 6.85 |
| Terbufos (15%) + phthalimide | 80 mg + 500 ppm | 32 | 14.57 | 4.16 |
| Terbufos (15%) + phthalimide | 160 mg + 500 ppm | 33 | 13.10 | 4.52 |
| Terbufos (15%) + phthalimide | 40 mg + 1000 ppm | 37 | 17.29 | 7.03 |
| Terbufos (15%) + phthalimide | 80 mg + 1000 ppm | 36 | 17.57 | 5.69 |
| Terbufos (15%) + phthalimide | 160 mg + 1000 ppm | 38 | 14.00 | 4.09 |
| Phthalimide | 500 ppm | 32 | 17.64 | 5.89 |
| Phthalimide | 1000 ppm | 33 | 17.42 | 5.92 |
| Control | 0 | 33 | 13.20 | 5.41 | tion at the rates shown in Table III. Pots are placed in a greenhouse and watered overhead for the duration of the experiment. Greenhouse temperatures run at 29° C. at day and 19° C. at night. Each treatment is replicated five times and compared to both negative controls, which are not treated, and positive controls which are treated with the herbicide or the phthalimide compound. After treatment, the plants are periodically rated for average ligule height by measuring the highest ligule of each plant and plant vigor on a scale of one to ten, with a rating of five being assigned to the untreated control, a rating of greater than five indicating greater vigor than the control and a rating of less than five indicating poorer vigor than the control.

The results of these experiments which are summarized in Table III.

compound. After treatment, the plants are periodically rated for average ligule height and vigor employing the rating system described in Example 3 hereinabove. The results of these experiments are summarized in Table IV.

TABLE IV

| | | IF | | Pre |
|---|---|---|---|---|
| Treatment | Rate | Avg ligule height (cm) (28 DAT)* | Plant vigor (28 DAT) | Plant vigor (18 DAT) |
| Untreated control | 0 | 7 | 5 | 5 |
| Pendimethalin | 0.25 kg/ha | 7.25 | 5 | — |
| Pendimethalin | 0.5 kg/ha | 6.0 | 3 | 3 |
| Pendimethalin | 1.0 kg/ha | 6.3 | 2 | 3 |
| Phthalimide | 500 ppm | — | — | 4 |
| Phthalimide | 1500 ppm | 8.25 | 5 | 6 |
| Pendimethalin + phthalimide | 0.25 kg/ha + 1500 ppm | 9.5 | 5 | — |
| Pendimethalin + phthalimide | 0.5 kg/ha + 1500 ppm | 8.25 | 5 | 5 |
| Pendimethalin + phthalimide | 1.0 kg/ha + 1500 ppm | 8.5 | 5 | 4 |

*DATS = Days after treatment

EXAMPLE 5

Efficacy and Safening of Treatments of the Invention when a Urea Herbicide is Used in Barley Seeds of winter barley, (Ponda), are treated with the phthalimide compound 1-(3-chlorophthalimido)cyclohexanecarboxamide at the rates indicated in Table V.

Test method: Five inch plastic pots are filled to within one inch of the top with greenhouse soil and leveled to a firm seed bed. Five seeds are placed on top of the leveled soil. The herbicide, isoproturon, is ap-

TABLE III

| | | Pre | | | IF | | PPI |
|---|---|---|---|---|---|---|---|
| Treatment | Rate | Avg ligule height (cm) (45 DAT*) | Plant vigor (18 DAT) | Plant vigor (45 DAT) | Ave ligule height (cm) (28 DAT) | Plant vigor (28 DAT) | Plant weight (gm) (13 DAT) |
| Untreated control | 0 | 41.6 | 5 | 5 | 11.25 | 5 | 10.1 |
| Pendimethalin | 1.5 kg/ha | 42.3 | 5 | 5 | 14.0 | 4 | 0.5 |
| Pendimethalin | 2.0 kg/ha | 44.6 | 4 | 4.5 | 13.25 | 3 | — |
| Phthalimide | 500 ppm | 48.9 | 7 | 5.25 | 13.5 | 5 | — |
| Phthalimide | 1000 ppm | 47.9 | 6 | 6 | 14.0 | 5 | 13.0 |
| Pendimethalin + phthalimide | 1.5 kg/ha + 500 ppm | 53.4 | 6 | 4.5 | 16.5 | 5 | — |
| | 2.0 kg/ha + 500 ppm | 51.4 | 6 | 4.5 | 16.75 | 4 | — |
| | 1.5 kg/ha + 1000 ppm | 50.8 | 6 | 5.25 | 17.5 | 5 | 9.2 |
| | 2.0 kg/ha + 1000 ppm | 48.3 | 6 | 5.25 | 15.25 | 4 | — |

*DAT = Days after treatment

EXAMPLE 4

Efficacy and Safening of Treatments of the Invention when a Dinitroaniline Herbicide is used in Sorghum Seeds of sorghum Dekalb 42Y, are treated with the phthalimide compound, 1-(3-chlorophthalimido)cyclohexanecarboxamide at the rates indicated in Table IV.

Test method: Five inch plastic pots are filled to within one inch of the top with greenhouse soil and leveled to a firm seed bed. Five seeds are placed on top of the leveled soil. The herbicide, pendimethalin, is applied as a spray to simulate preemergence (Pre), and in furrow applications as shown in Table IV. Pots are placed in a greenhouse and watered overhead for the duration of the experiment. Greenhouse temperatures run at 29° C. in day at 19° C. at night. Each treatment is replicated five times and compared to both negative controls, which are not treated, and positive controls which are treated with the herbicide or the phthalimide compound.

plied as a spray to simulate a preplant incorporated application shown in Table V. Pots are placed in a greenhouse and watered overhead for the duration of the experiment. Greenhouse temperatures run at 24° C. and 16° C. at night. Each treatment is replicated five times and compared to both negative controls, which are not treated, and positive controls which are treated with the herbicide or the phthalimide compound. Twelve days after treatment, the plants are rated for stand by counting the plants, and a percent stand is calculated ligule heights are averaged. The results of these experiments are summarized in Table V.

TABLE V

| Treatment | Rate | Stand % | Average ligule height (cm) |
|---|---|---|---|
| Untreated control | 0 | 93 | 3.05 |
| Isoproturon | 3 kg/ha | 67 | 2.30 |
| Phthalimide | 1000 ppm | 87 | 5.45 |
| Isoproturon + | 3 kg/ha + 1000 ppm | 93 | 6.30 |

TABLE V-continued

| Treatment | Rate | Stand % | Average ligule height (cm) |
|---|---|---|---|
| phthalimide | | | |

What is claimed is:

1. A method for protecting crop plants from undesirable phytotoxic effects caused by terbufos, said method comprising: applying to the roots, seeds or the soil surrounding said crop plants or to the foliage of said crop plants an effective plant protecting amount of 1-(3-chlorophthalimido) cyclohexanecarboxamide in conjunction with applying an insecticidally effective amount of terbufos at a rate which is phytotoxic to said crop plants.

2. The method according to claim 1, wherein the effective plant protecting amount of 1-(3-chlorophthalimido) cyclohexanecarboxamide is 500 ppm to 1,000 ppm.

3. A composition for protecting crop plants from undesirable phytotoxic effects caused by terbufos, said composition comprising: an effective plant protecting amount of 1-(3-chlorophthalimido) cyclohexanecarboxamide and a phytotoxic, insecticidally effective amount of terbufos.

* * * * *